United States Patent
Vogt et al.

(10) Patent No.: US 8,043,003 B2
(45) Date of Patent: Oct. 25, 2011

(54) METHOD FOR DETERMINING AN IMAGING RULE AND METHOD FOR GENERATING A 3D RECONSTRUCTION

(75) Inventors: Florian Vogt, Effeltrich (DE); Holger Kunze, Bubenreuth (DE); Benno Heigl, Coburg (DE)

(73) Assignee: Siemens Aktiengesellschaft, Munich (DE)

( * ) Notice: Subject to any disclaimer, the term of this patent is extended or adjusted under 35 U.S.C. 154(b) by 549 days.

(21) Appl. No.: 12/231,664

(22) Filed: Sep. 4, 2008

(65) Prior Publication Data
US 2009/0067583 A1   Mar. 12, 2009

(30) Foreign Application Priority Data
Sep. 6, 2007   (DE) .................... 10 2007 042 333

(51) Int. Cl.
  *A61B 6/03* (2006.01)
(52) U.S. Cl. .......................................... 378/207; 378/4
(58) Field of Classification Search ............. 378/4, 98.8, 378/207; 382/131
  See application file for complete search history.

(56) References Cited

U.S. PATENT DOCUMENTS

| | | | |
|---|---|---|---|
| 5,442,674 A | 8/1995 | Picard et al. | |
| 5,963,612 A | 10/1999 | Navab | |
| 5,963,613 A | 10/1999 | Navab | |
| 6,044,132 A | 3/2000 | Navab | |
| 6,731,283 B1 | 5/2004 | Navab | |
| 2004/0013240 A1 | 1/2004 | Mitschke et al. | |
| 2006/0039537 A1* | 2/2006 | Strobel | 378/197 |
| 2007/0122020 A1* | 5/2007 | Claus et al. | 382/131 |

FOREIGN PATENT DOCUMENTS

| | | |
|---|---|---|
| DE | 19858306 A1 | 7/1999 |
| DE | 10215808 B4 | 11/2003 |
| DE | 10 2006 041 033 | 3/2008 |
| FR | 2881941 A1 * | 8/2006 |

OTHER PUBLICATIONS

Gorges et al., 3D Augmented Fluoroscopy in interventional Neuroradiology: Precision Assessment and First Evaluation on Clinical Cases, 2006, Proceeding of MICCAI06, Workshop on Augmented environments for Medical Imaging and Computer-aided Surgery—AMI-ARCS 2006, 10 Pages.*

Khamene et al., Automatic registration of portal images and volumetric CT for patient positioning in radiation therapy, 2006, Medical Imaging Analysis, vol. 10, pp. 96-112.*

(Continued)

*Primary Examiner* — Edward Glick
*Assistant Examiner* — John Corbett

(57) ABSTRACT

It is possible that at a predetermined position of the imaging components of a radiographic imaging system the object is not fully viewed. The object can be a calibration phantom, which means that it is not possible to directly determine an imaging rule with the aid of the calibration phantom at this position of the imaging components. According to the invention, an imaging of the calibration phantom at a different position takes place and an imaging rule for this position is determined. This is then converted, provided a movement parameter is known which describes the movement from the position with the record of the calibration phantom to a different position. The imaging rule obtained in this way can be further improved, e.g. with the aid of a recording of the calibration phantom from the position in question, including if the calibration phantom is not completely imaged.

15 Claims, 1 Drawing Sheet

OTHER PUBLICATIONS

Hoppe, Calibration of the Circle-plus-Arc Trajectory, 2006 IEEE Nuclear Science Symposium Conference Record, pp. 2913-2918.*
Muller et al., Correction of C-Arm Projection Matrices by a 3D-2D Rigid Registration of CT-Images Using Mutual Information, 2003, Lecture Notes in Computer Science (LNCS), Proceedings of the Second International Workshop on Biological Image Registration (WBIR 2003), LNCS vol. 2717, pp. 161-170.*
Lavest et al., Do We Really Need an Accurate Calibration Pattern to Achieve a Reliable Camera Calibration?, 1998 Computer Vision—ECCV'98, Lecture Notes in Computer Science, vol. 1408, pp. 158-174.*
William H. Press, Saul A. Teukolsky, William T. Vetterling and Brian P. Flannery; Numerical Recipes in C. The art of scientific computing Kapitel 15.5—Nonlinear Models Press et al.; pp. 681-688; Book; 1992.
Levenberg-Marquardt-Algorithmus aus Wikipedia, der freien Enzyklopädie Zeitpunkt der Bearbeitung: 22:11, 28. Jun. 2007 durch AlleborgoBot; Others; 2007; siehe # 2.
Strobel et al., "Improving 3D Image Quality of X-Ray C-Arm Imaging Systems by Using Properly Designed Pose Determination Systems for Calibrating the Projection Geometry,", Medical Imaging 2003, Physics of Medical Imaging, Proceedings of the SPIE, 2003, pp. 943-954, vol. 5030, Edited by M.J. Yaffe, L.E. Antonuk.

* cited by examiner

FIG 1
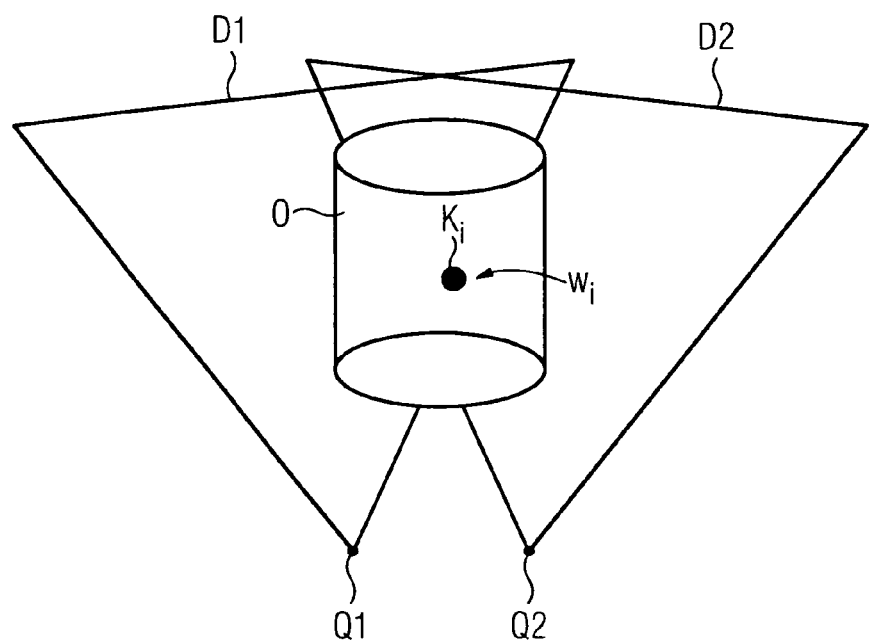
FIG 2         FIG 3         FIG 4
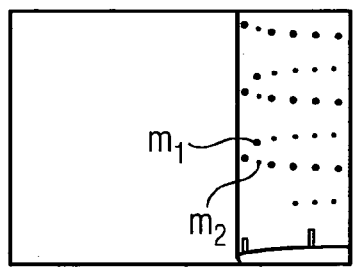 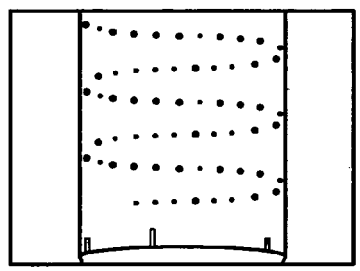 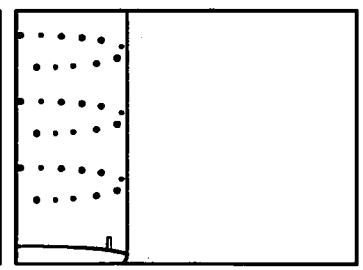

METHOD FOR DETERMINING AN IMAGING RULE AND METHOD FOR GENERATING A 3D RECONSTRUCTION

CROSS REFERENCE TO RELATED APPLICATIONS

This application claims priority of German application No. 10 2007 042 333.2 filed Sep. 6, 2007, which is incorporated by reference herein in its entirety.

FIELD OF THE INVENTION

The invention relates to a method for determining an imaging rule for imaging points in the 3D space on points in a 2D X-ray image at any positions of the imaging components of a radiographic imaging system, i.e. those components with whose help the 2D X-ray image is generated. Knowledge of such a rule is necessary, especially for a method for generating a 3D reconstruction of a body located in a radiographic imaging system, with the reverse image then normally being used for the 3D reconstruction.

BACKGROUND OF THE INVENTION

The relevant area of expertise has long been engaged in determining imaging rules. U.S. Pat. Nos. 5,963,612 and 5,963,613 are examples of this. The imaging rule is normally determined with the aid of a "calibration phantom". Such a calibration phantom has pre-determined structural elements that are reflected in certain structures in an X-ray image of the calibration phantom and the imaging rule can be deduced from these imaged structures. U.S. Pat. No. 6,044,132 describes an example of a calibration phantom. A different calibration phantom is described in the article by N. Strobel, B. Heigl, T. Brenner, O. Schutz, M. Mitschke, K. Wiesent, T. Mertelmeier, entitled "Improving 3D image quality of X-ray C-arm imaging systems by using properly designed posed determination systems for calibrating the projection geometry, Medical Imaging 2003", and was published in the year 2003 in the book entitled "Physics of Medical Imaging" by Yaffe, Martin J., Antonuk, Larry E., Proceedings of the SPIE, Vol. 5030, pages 943 to 954.

A precondition to enable the imaging rule to be determined with the aid of an image of a calibration phantom is normally that a minimum amount of the structural elements can be imaged in the X-ray image. If the calibration phantom is placed on the patient table, this means that the determination of an imaging rule at any positions of the imaged components as required is not possible. At some positions, the amount of the calibration phantom that can be recorded is so small that a determination of an imaging rule is not possible. This problem is shown sharply with the method described in DE 10 2007 026 115.4, published after the date of filing of this application. The object of this method is to generate a 3D reconstruction of a particularly large body, which cannot be recorded by a single projection. To solve the problem, at least two projections (X-ray images), each of which records part of the body, are taken at each position of an X-ray C-arm, but, overall, each structure of the body is recorded on one of the two projections. DE 10 2007 026 115.4 is concerned with the problem that the real sources Q1 and Q2 do not coincide with both projections. After filtering with the aid of a virtual detector, the imaging rules, which have lead to both projections (i.e. both X-ray images), are used reversed and individually in a filtered back-projection to generate the 3D reconstruction. With the method from DE 10 2007 026 115.4, it is therefore necessary to determine the imaging rule for both positions of the imaging components at which both X-ray images were taken. Because these positions are chosen so that the particularly large body is imaged in the border area in each case and the border area is covered anyway, the X-ray images are individually recorded, i.e. each on its own, from a particularly unusual perspective. If a calibration phantom is placed on the patient table, this is only approximately half covered in each case. If the calibration phantom from the article by Strobel et al. is used, this would make the determination of the imaging rule impossible on the basis of a single X-ray image alone.

SUMMARY OF THE INVENTION

The object of the invention is to provide a method for determining an imaging rule for the imaging of points in the 3D space on points in a 2D X-ray image and to enable this to be achieved at any positions of the imaging components of the radiographic imaging system, i.e. so that there are no limitations with respect to the position at which the imaging rule is to be determined.

The object is achieved by a method with the features according to the claims.

The inventive method therefore includes the following steps
a) Defining any position of the imaging components of the radiographic imaging system as an actual imaging position.
b) Providing a calibration phantom with predetermined structural elements and bringing said calibration phantom into the radiographic imaging system.
c) Defining a calibration imaging position of the imaging components of the radiographic imaging system at which the calibration phantom present in the radiographic imaging system is adequately and completely mapped, so that an imaging rule can be determined for the calibration imaging position.
d) Recording an X-ray image of the calibration phantom as a calibration image at the calibration imaging position.
e) Determining the imaging rule for the calibration imaging position.
f) Recording the process parameters describing the movement from the calibration imaging position to the actual imaging position.
g) Using the recorded movement parameters to convert the calibration imaging position to a preliminary valid or (even) final imaging rule for the actual imaging position.

To sum up, a position of the imaging components is sought at which an imaging rule can be determined and the imaging rule thus determined can then be converted.

An imaging rule usually includes extrinsic parameters, i.e. a rotary matrix, which describes the rotation of the imaging components, a translation vector, which describes the movement of the imaging components, and in fact does all this relative to the system of coordinates in which the imaging rule is described. An image is again applied to this rotary matrix and translation vector, with said image containing the intrinsic parameters, which describes the properties of the imaging components, such as the distance of the X-ray detector from the focal plane, i.e. a variable which describes the distance setting of the X-ray detector, or also a variable such as the pixel size relative to this distance. In a simplest case, the calibration imaging position is chosen so that it is produced in one rotation from the actual image position. The imaging rule can then be simply converted in that a rotary matrix that describes the rotation about the movement angle from the calibration imaging position to the actual imaging position is placed in front of the rotary matrix containing the extrinsic parameters.

In an ideal case, the desired imaging rule is exactly obtained by the conversion of the one imaging rule to the desired imaging rule. However, actual radiographic imaging systems have characteristics which cause deviations. Thus, it can be that when a certain movement angle is programmed-in the actual movement angle deviates from it. The deviation between the nominal movement angle and the movement angle must then be allowed for in the imaging rule. The result of this is that the imaging rule determined in step g) by conversion is seen only as a preliminary valid imaging rule, which must be subjected to further process steps. With a preferred form of embodiment, a correction takes place by using an X-ray image of the calibration phantom present in the radiographic imaging system at the actual imaging position (which is regarded as step h) during the continuation of the process), with this X-ray image being subsequently evaluated. Furthermore, the method according to this step h) contains, for example, the following steps j) Assigning of structures in the X-ray image taken in step h) to the structural elements of the calibration phantom.

k) Calculating how the structural elements of the calibration phantom would be imaged if the preliminary valid imaging rule were correct, and determining properties of these calculated images of the structural elements.

l) Comparing the properties of the calculated images with the properties of the structures in the X-ray image assigned in step j). Defining a degree of agreement and changing the preliminary valid imaging rule to increase the match according to the degree of agreement, and preferably optimizing the match at least under predetermined secondary conditions (e.g. a typical step size when changing or with the secondary condition of an abort criterion as part of the change).

The first approximation, i.e. the preliminary valid imaging rule, is thus compared with the actual image and the preliminary valid imaging rule is then corrected using the actual image. It should again be pointed out that this present invention assumes that the X-ray image taken in step h) is on its own not sufficient for the derivation of the imaging rule. The calibration image taken at the calibration imaging position is required for this. The X-ray image taken in step h) can, however, contain a sufficient amount of information to enable an effective correction of the preliminary valid imaging rule to be carried out.

Spherical structural elements are frequently used as the structural elements of the calibration phantom.

In the case of Strobel et al., in the calibration phantom described in the aforementioned article, the spheres are of different diameters so that at least adjacent spheres in the X-ray image can differ from each other.

The centre points of the circle forming the sphere can then be used as a property of the structures depicted in the X-ray images, i.e. of the circles in the X-ray image taken in step h) or of the circles of the image to be calculated in step k). Different X-ray image coordinates are thus obtained from the X-ray image h) and calculation imaging coordinates are obtained from the virtual X-ray image calculated in step k), and these can be placed in relation to each other. The simplest criterion is to calculate the distance between the X-ray image coordinate and the associated calculation image coordinate. This distance can also be used as the criterion for the optimization of the imaging rule, and in fact the sum of the smallest squares of these distances of the X-ray image coordinate from the associated calculated image coordinate is used. Any method of non-linear optimization can be used. Levenberg-Marquardt optimization has proven to be particularly appropriate.

Before optimizing with the aid of the criterion of the sum of the smallest squares of the distances, it should be guaranteed that the assignment made in step j) is completely reliable. The assignment from step j) can also be regarded as a first preliminary and then optimized during step l) in that the imaging rule is corrected by a translation, which just means that the calculated image is moved as a mask over the X-ray image taken in step h) until the greatest possible agreement of the assignment is obtained. This also can take place according to a predetermined degree of agreement. For example, the translation can take place in predetermined steps and the sum of the smallest squares of the distances of the X-ray coordinates from the associated calculated image coordinates (last translated) calculated at each step. The number of assigned elements can also simply be used as a predetermined degree of agreement. This is then appropriate if the structures are arranged so that the individual structures cannot be assigned. In this case, the particular assignment at which most structural elements of the calibration phantom can be assigned is then sought.

As already mentioned above, the imaging rule includes extrinsic and intrinsic parameters. The matching of the imaging rule certainly does not have to extend to all parameters. It is possible to change just the parameters of the one kind in step l) with the other parameters remaining the same. In particular, in this case changing the extrinsic parameters, which belong to the imaging rule, in step l) and not changing the intrinsic parameters can be considered. It is assumed that the properties of the detector absolutely do not change due to the tilting (i.e. the method using the movement parameters).

In cases of doubt, the intrinsic parameters can, of course, also be matched, i.e. both the parameters of a first and of a second type can be changed in the course of step l).

It can now be that, as before, the assignment of structures in the X-ray image taken in step h) to the structural elements of the calibration phantom according to step j) does not take place reliably. The reason for this can be that the X-ray image taken in step h) does not depict an adequate number of structural elements of the calibration phantom. A solution to this is changing the position and imaging the remaining structures separately. This is carried out in that a complementary position of the imaging components of the radiographic imaging system is defined according to step h') in such a way that when taking an X-ray image of the calibration phantom located in the radiographic imaging system both those structures are imaged that are not imaged in the X-ray image taken in step h) and the structures in the X-ray image taken in step h) are also imaged. In this complementary position, an X-ray image is then accordingly taken. The complementary position can, for example, be the corresponding position in the second projection, if the method from DE 10 20007 026 115.4 is used, if the actual imaging position is the position during the first projection. In this case, in the course of step j) the X-ray image taken in step h') is registered to the X-ray image taken in step h), i.e. correctly assigned according to position and dimensions, which just means that an imaging rule from the one X-ray image to the other X-ray image is obtained. Based on this imaging rule, i.e. based on the assignment, image h) can be expanded in order to thus be able to assign the structures in the expanded X-ray image to the structures of the calibration phase (and therefore the assignment of the structures in the non-expanded X-ray image from step h) can be effected more accurately). With this embodiment of the method, it is therefore necessary that the calibration imaging position be necessarily defined so that a preliminary valid imaging rule can really be obtained, and the X-ray image taken in step h) is then supplemented by the X-ray image taken in h') so that the preliminary valid imaging rule can be optimized.

According to an aspect of the invention, the previously described method for determining an imaging rule for imaging points in 3D space on points in a 2D X-ray image is used as part of a process for generating a 3D reconstruction of a body located in a radiographic imaging system, with the method used for determining an imaging rule being equally performed twice and with, in step a), different actual imaging positions being defined in each case, which expand so that each structure of the body located in the radiographic imaging system is imaged in at least one X-ray image, which is imaged at one of the actual imaging positions. The imaging rules obtained in the process are reversed, i.e. in an image from a 2D X-ray image to the 3D space and the back projection rules obtained in this way are used to actually back project the X-ray images obtained in the actual imaging positions and thus generate the 3D reconstruction. The method according to Claim 9 can especially be the method described in the aforementioned DE 10 2007 026 115.4, with which the recorded X-ray images are filtered with the aid of a virtual detector.

BRIEF DESCRIPTION OF THE DR

A preferred embodiment of the invention is described in the following with reference to the drawings, in which;

FIG. 1 shows two different complementary positions of the imaging components of a radiographic imaging system showing the overall complete imaging of a body, FIG. 2 shows the image of a calibration phantom taken at a first of the positions from FIG. 1, FIG. 3 shows the image of the calibration phantom taken at a second position, FIG. 4 shows the image of the calibration phantom shown at the second position from FIG. 1.

DETAILED DESCRIPTION OF THE INVENTION

DE 10 2006 041033.5 describes how two different X-ray images are taken, which together cover the body, for the generation of a 3D reconstruction of a particularly large body, which cannot be imaged by a single projection. The X-ray detector is tilted between the taking of the two X-ray images. Basically, it is assumed that the X-ray radiation source remains at the same location, but this can also move in an actual radiographic imaging system. DE 10 2007 026 115.4 deals with the latter case and this is also shown in FIG. 1. In this case, an X-ray radiation sources Q1 radiates X-ray radiation on to an X-ray detector D1 and in a second position the X-ray source Q1 has moved to a point different from the X-ray source Q2, and the detector D1 has moved in a different plane and is therefore designated as D2. The method according to DE 10 2007 026 115.4 requires an imaging rule for the imaging of points in the 3D space on points in a 2D X-ray image, i.e. on the detectors D1 and D2. Normally, a "calibration phantom", is used in order to derive this imaging rule. In FIG. 1, a calibration phantom is symbolically shown as object O. It is assumed that a calibration phantom used here is the calibration phantom known from the article by Strobel et al., mentioned in the introduction. In this case, a sequence of metal spheres is arranged in the shape of a spiral in a cylindrical Plexiglas body. The size of the metal spheres varies. If a sequence of eight spheres can be identified in the X-ray image, an assignment of the spheres to images of spheres is certainly possible.

FIG. 2 now shows an X-ray image of the object O taken with the aid of the detector D1 with X-ray radiation transmitted by the X-ray source Q1. FIG. 4 shows the X-ray image taken with the aid of detector D2 with X-ray radiation emitting from the source Q2. It can be clearly seen that the X-ray images do not completely show the object O, i.e. the calibration phantom, which makes the determination of an imaging rule difficult if not even impossible. The imaging rules that lead to the generation of X-ray images according to FIG. 2 or FIG. 4 must, however, be known. This is aided in that an additional X-ray image of the calibration phantom O is taken. This is shown in FIG. 3. A property of the X-ray image is that the calibration phantom O is adequately and completely shown, so that an imaging rule is determined. In the case of the embodiment according to FIG. 1, it has been shown that an X-ray image as shown in FIG. 3 is obtained in an intermediate position of the two positions. If the detector is tilted from detector position D1 to D2 by an angle, it must be tilted by an angle $2\alpha$ to retain the position in which the X-ray image according to FIG. 3 can be taken. It should be pointed out that both positions from FIG. 1 are defined so that a largest possible body, which cannot be completely imaged by a single image, is altogether completely imaged. The calibration phantom O can, however, be smaller than this large body and is actually practically completely imaged in FIG. 3.

The imaging rule which one obtains usually (see U.S. Pat. No. 6,044,132) has the following form $$P = (KR^T | KR^T t) \quad (1)$$

In this case P is a 3×4 matrix that can be used on a quad vector, which describes a spatial point. The spatial point usually has three dimensions. This can be described by a quad vector, which describes homogenous coordinates. The imaging takes place on a triple vector, which reproduces a point on a 2D X-ray image in homogenous coordinates. The matrix R is a 3×3 rotary matrix and t is a translation vector with three entries. The matrix R and the translation vector t contain the so-called extrinsic coordinates. These are the coordinates which, relative to the coordinates system to which the projection P is described, reflect the shift (translation vector t) and rotation (rotation matrix R). Part of the projection P, after application of the rotary matrix, and partially also of the translation vector t, to the entries of the vector describing the one point in the 3D space, is to still allow a matrix K to act. The matrix K is a 3×3 matrix and reflects the influence of the detector properties. These are especially the distance from the source to the image and the size of the imaging elements (pixels) relative to this distance.

As mentioned above, the detector D1 was rotated by an angle $\alpha$ in order to obtain the image according the FIG. 3 leading to the imaging rule P. The imaging rule $P_1$ is now required for the system from source Q1 and detector D1. This is obtained in a first approximation by a simple application of a rotary matrix with an angle of rotation $\alpha$ to the rotary matrix R, which results in the following $$P_1 = (KR(\alpha)R^T | KR(\alpha)R^T(t+\Delta t)) \quad (2)$$

$\Delta t$ is a translation vector which describes the translation between the positions and in this case is preferred to be equal to zero. $P_1$ should in this case be a first approximation, which is subject to further steps.

The image from FIG. 2 is used for these further steps. A part of the calibration phantom O in this case is also shown. Although the individual structures in the X-ray image from FIG. 2 can possibly not be identified from this, identification is however possible by comparing the actual structures with structures from a calculated X-ray image, provided the above imaging rule $P_1$ is used.

$P_1$ is simply applied to the structural elements of the calibration phantom O. A sphere $K_i$ of the calibration phantom O is shown as an example in FIG. 1. It is assumed that the centre point has the coordinate $w_i$, with this being described by a 4D vector $$w_i = \begin{pmatrix} w_{ix} \\ w_{iy} \\ w_{iz} \\ 1 \end{pmatrix} \quad (3)$$

If $P_1$ is now applied to this 4D vector a 3D vector corresponding to the following is obtained.

$$\begin{pmatrix} p_{1ix} \\ p_{1iy} \\ p_{1iz} \end{pmatrix} = P_1 w_i. \quad (4)$$

If the following is defined $$f(P_1, w_i) = \begin{pmatrix} p_{1ix}/p_{1iz} \\ p_{1iy}/p_{1iz} \end{pmatrix}, \quad (5)$$

we then get $$q_i = f(p_1, w_i) \quad (6).$$

This is calculated for i=0, ..., 107 for 108 spheres of the calibration phantom O corresponding to the article by Strobel et al.

$q_i$ are now image coordinates in the image that can be taken with the aid of source Q1 and detector D1 together, if $P_1$ were the correct imaging rule. The $q_i$ are then compared with the actual structures in FIG. 2, with the different spheres $K_i$ being depicted as small circles in FIG. 2, which can be assigned to the centre point coordinate $m_j$.

In order to have a measure for the quality of the imaging rule $P_1$, the $q_i$ must now be clearly assigned to $m_j$. In doing so it is necessary to avoid assigning the structures with the centre points $m_j$ from FIG. 2 to the incorrect spheres $K_i$.

With a simple embodiment the particular nearest $q_i$ is simply sought for each $m_j$. The following formula thus applies.

$$l(j) = \operatorname{argmin}_i(\|q_i - m_j\|), i = 0, \ldots, 107 \quad (7)$$

To increase reliability, the secondary condition, i.e. that the maximum distance is θ according to $$\|q_i - m_j\| \leq \theta \quad (8).$$

can be used in this case. When the calibration phantom according to Strobel et al. is used, an additional criterion can be that the size of the structure whose centre point is $m_j$ corresponds to the size of the spheres $K_i$ that are to be assigned. If there are two different sphere sizes, there are also two different circle sizes (simply: "large" or "small") in the illustration in FIG. 2.

If the process does not lead to a satisfactory assignment, it is possible to additionally introduce a translation. It can be that the above formula (2) does not provide the translation with adequate precision. Formula (2) already includes a change in the translation vector by the value Δt. It can now be that in the actual system an additional translation is necessary. A test can be made for the coordinates $m_j + k_x \Delta x + k_y \Delta_y$, with $\Delta_x, \Delta_y$ being typical coordinate distances and with $k_x, k_y = \ldots -3, -2, -1, 0, 1, 2, 3$, etc. A calculation can then be made as follows for each such translation $$l(j, k_x, k_y) = \operatorname{argmin}_i(\|q_i - (m_j + k_x \Delta_x + k_y \Delta_y)\|). \quad (9)$$

The particular pair $(k_x, k_y)$ can be selected for which a predetermined secondary condition applies, e.g. for which the most assignments were achieved. The final value for $(k_x, k_y)$ can also be that value that minimizes the sum of the squares of the distances between the assigned calculated and actual circle centre points, with the latter being shifted by the multiple of $\Delta_x, \Delta_y$. Accordingly, formulae (10a/10b) then, for example, apply as a secondary condition:

$$k_x = \arg_n \min \left( \sum_j \|q_{l(j,n)} - (m_j + n\Delta_x)\|^2 \right) \quad (10a)$$

$$k_y = \arg_p \min \left( \sum_j \|q_{l(j,n)} - (m_j + k_x \Delta_x + p\Delta_y)\|^2 \right) \quad (10b)$$

After an optimum assignment of this kind has now been achieved, the assignment of $q_{1(j)}$ for matching $P_1$ can be used, with the extrinsic parameters contained in R and t being subjected to an optimization process. In this case also the criterion of the smallest square distances (in total) can be used, with the size f(k), thus being minimized and the following applying:

$$f(k) = \sum_j \|q_{l(j)} - (m_j + k_x \Delta_x + k_y \Delta_y)\|^2. \quad (11)$$

In a case where a check was not carried out during the assignment step to determine whether a translation of the calculated image was necessary, $k_x = 0 = k_y$ applies in any case.

Optimization can taken place in accordance with Levenberg-Marquardt or also according to any other non-linear optimization process.

Normally, only the extrinsic parameters from the variables R and t are matched. The method does not, however, rule out the intrinsic parameters from the matrix K being matched.

The above steps of the method are then always valid regardless of the situation according to FIG. 1 if the imaging rule is determined at a position at which normally the calibration phantom is not completely recorded (e.g. in the usual situation where it is placed on the patient table). The additional record is then taken, the imaging rule is obtained from the additional image, the imaging rule is converted to an imaging rule for the position in question and, if necessary, the imaging rule is then adapted using X-ray images for the position in question.

In the method according to DE 10 2007 026 115.4, a second position is available (see X-ray source Q2 in detector D2 in FIG. 1). This can be used to take a further image of the calibration phantom, i.e. the image shown in FIG. 4. A registration step of the two X-ray images of the calibration phantom, in which this is only partially shown, can be carried out, with the images from FIG. 2 and FIG. 4 being registered relative to each other. By means of this registration, i.e. by an assignment of the coordinates systems with respect to the correct position and dimensions, an imaging rule is obtained from the X-ray image from FIG. 4 with respect to the X-ray image from FIG. 2 (or vice versa) and can thus expand the X-ray image from FIG. 2. In this way the correct assignment of the circle centre point $m_j$ to the spheres $K_i$ can be simplified or perhaps even enabled.

The invention claimed is:

1. A method for determining an imaging rule at a position of imaging components of a radiographic imaging system, comprising:
    defining a first position of the imaging components as an actual imaging position;
    positioning a calibration phantom with a structural element into the radiographic imaging system at which the calibration phantom is at least partially imaged in X-ray images taken from the actual imaging position;
    defining a calibration imaging position of the imaging components at which the calibration phantom is completely imaged;
    taking X-ray images of the calibration phantom at the calibration imaging position and at the actual imaging position;
    determining an imaging rule at the calibration imaging position;
    detecting a movement process from the calibration imaging position to a movement parameter in the actual imaging position;
    converting the imaging rule at the calibration imaging position to the imaging rule at the actual imaging position based on the movement parameter;
    defining a complementary position of the imaging components for the actual imaging position such that the X-ray image of the calibration phantom at the calibration imaging position comprises both the structure element that is imaged and not imaged in the X-ray image taken at the actual imaging position;
    taking an X-ray image at the complementary position;
    registering the X-ray image taken at the complementary position with the X-ray image taken actual imaging position; and
    assigning a structure in the registered X-ray image to the structural element of the calibration phantom.

2. The method as claimed in claim 1, wherein the imaging rule at the actual imaging position is a preliminary valid imaging rule.

3. The method as claimed in claim 2, further comprising:
    assigning a structure in the X-ray image taken at the actual imaging position to the structural element of the calibration phantom;
    calculating an image based on how the structural element of the calibration phantom is imaged when the preliminary valid imaging rule is correct;
    determining a property of the structural element in the calculated image;
    comparing the property of the structural element with a property of the assigned structure in the X-ray image taken at the actual imaging position;
    defining a degree of agreement based on the comparison; and
    changing the preliminary valid imaging rule to increase the agreement in accordance with the degree of agreement.

4. The method as claimed in claim 3, wherein the calibration phantom comprises a plurality of spheres.

5. The method as claimed in claim 4, wherein the property of the structural element and the property of the assigned structure in the X-ray image are X-ray image coordinates of centre points of circles of the spheres in the X-ray image taken at the actual imaging position.

6. The method as claimed in claim 5, wherein the property of the structural element and the property of the assigned structure are calculated image coordinates of centre points of circles of the spheres in the calculated image.

7. The method as claimed in claim 6, wherein the preliminary valid imaging rule is optimized according to a criterion of smallest squares of distances between the X-ray image coordinates to the calculated image coordinates associated.

8. The method as claimed in claim 7, wherein the preliminary valid imaging rule is optimized by Levenberg-Marquardt optimization.

9. The method as claimed in claim 6, wherein the preliminary valid imaging rule is first corrected by a translation according to a predetermined degree of agreement and is subsequently optimized according to a criterion of a sum of smallest squares of distances between the X-ray image coordinates to the calculated image coordinates associated.

10. The method as claimed in claim 2, wherein the imaging rule is defined by two types of parameters of the imaging components and only one type of the parameters is changed in changing the preliminary valid imaging rule to increase the agreement in accordance with the degree of agreement.

11. The method as claimed in claim 2, wherein the imaging rule is defined by two types of parameters of the imaging components and both the two types of the parameters are changed in changing the preliminary valid imaging rule to increase the agreement in accordance with the degree of agreement.

12. The method as claimed in claim 1, wherein the imaging rule is used for determining an imaging point in a three-dimensional (3D) space on a point in a two-dimensional (2D) X-ray image.

13. The method as claimed in claim 12, wherein two actual imaging positions for the imaging components are defined for determining two image rules at the two respective actual imaging positions.

14. A method for determining an imaging rule at a position of imaging components of a radiographic imaging system, comprising:
    defining a first position of the imaging components as an actual imaging position;
    positioning a calibration phantom with a structural element into the radiographic imaging system at which the calibration phantom is at least partially imaged in X-ray images taken from the actual imaging position;
    defining a calibration imaging position at which the calibration phantom is completely imaged;
    taking X-ray images at the calibration imaging position and at the actual imaging position;
    determining an imaging rule at the calibration imaging position;
    detecting a movement process from the calibration imaging position to a movement parameter in the actual imaging position; and
    converting the imaging rule at the calibration imaging position to the imaging rule at the actual imaging position based on the movement parameter,
    wherein the imaging rule is used for determining an imaging point in a three-dimensional (3D) space on a point in a two-dimensional (2D) X-ray image;

wherein two actual imaging positions for the imaging components are defined for determining two image rules at the two respective actual imaging positions; and wherein a 3D reconstruction of the 2D X-ray image is generated by reversing the two image rules in back projecting the 2D X-ray image in the 3D space.

15. A method for generating a three-dimensional (3D) reconstruction of a two-dimensional (2D) X-ray image taken by a radiographic imaging system, comprising:

defining two positions of imaging components of the radiographic imaging system as two actual imaging positions for obtaining X-ray images of a large body;

providing and positioning a calibration phantom with a structural element at which the calibration phantom is partially imaged in the X-ray images of the large body at each of the actual imaging positions;

defining a third position comprising a calibration imaging position of the imaging components intermediate of the two actual imaging positions at which the calibration phantom is completely imaged;

recording X-ray images of the calibration phantom at the calibration imaging position and at each of the actual imaging positions;

determining an imaging rule at the calibration imaging position;

detecting a movement process from the calibration imaging position to a movement parameter at each of the actual imaging positions;

converting the imaging rule at the calibration imaging position to an imaging rule at each of the actual imaging positions based on the movement parameter; and generating the 3D reconstruction by back projecting the 2D X-ray image in a 3D space via reversing the imaging rule at each of the actual imaging positions.

* * * * *